(12) United States Patent
Santi et al.

(10) Patent No.: US 7,541,330 B2
(45) Date of Patent: Jun. 2, 2009

(54) CONJUGATES WITH REDUCED ADVERSE SYSTEMIC EFFECTS

(75) Inventors: Daniel V. Santi, San Francisco, CA (US); Brian Hearn, San Francisco, CA (US)

(73) Assignee: Kosan Biosciences Incorporated, Princeton, NJ (US)

( * ) Notice: Subject to any disclaimer, the term of this patent is extended or adjusted under 35 U.S.C. 154(b) by 303 days.

(21) Appl. No.: 11/149,758

(22) Filed: Jun. 9, 2005

(65) Prior Publication Data

US 2005/0287155 A1 Dec. 29, 2005

Related U.S. Application Data

(60) Provisional application No. 60/580,142, filed on Jun. 15, 2004.

(51) Int. Cl.
*A61K 38/00* (2006.01)
*C07K 16/00* (2006.01)
*A61K 39/395* (2006.01)

(52) U.S. Cl. .................... 514/2; 530/350; 530/387.1; 530/388.1; 530/388.26; 530/389.8; 530/402; 424/130.1; 424/134.1

(58) Field of Classification Search .................... 514/2; 530/350, 387.1, 388.1, 388.26, 389.8, 402; 424/130.1, 134.1
See application file for complete search history.

(56) References Cited

U.S. PATENT DOCUMENTS

| | | | |
|---|---|---|---|
| 4,558,139 A | 12/1985 | Hagenmaier et al. | |
| 4,631,190 A | 12/1986 | Shen et al. | |
| 4,771,070 A * | 9/1988 | Hokanson et al. | 514/460 |
| 4,952,394 A | 8/1990 | Senter | |
| 5,137,877 A | 8/1992 | Kaneko et al. | |
| 5,144,011 A | 9/1992 | Shen et al. | |
| 5,354,773 A | 10/1994 | Herslof et al. | |
| 5,416,064 A | 5/1995 | Chari et al. | |
| 5,708,146 A | 1/1998 | Willner et al. | |
| 5,824,805 A | 10/1998 | King et al. | |
| 5,846,545 A | 12/1998 | Chari et al. | |
| 5,856,571 A | 1/1999 | Berninger et al. | |
| 5,869,045 A | 2/1999 | Hellstrom et al. | |
| 5,880,270 A | 3/1999 | Berninger et al. | |
| 5,980,896 A | 11/1999 | Hellstrom et al. | |
| 6,008,203 A | 12/1999 | Magnani et al. | |
| 6,214,345 B1 | 4/2001 | Firestone et al. | |
| 6,281,202 B1 | 8/2001 | Magnani et al. | |
| 6,333,410 B1 | 12/2001 | Chari et al. | |
| 6,372,712 B1 | 4/2002 | Briesewitz et al. | |
| 6,436,931 B1 | 8/2002 | Chari et al. | |
| 6,441,163 B1 | 8/2002 | Chari et al. | |
| 6,562,785 B1 * | 5/2003 | Shapiro | 514/9 |
| 6,759,509 B1 | 7/2004 | King et al. | |
| 2003/0055226 A1 | 3/2003 | Chari et al. | |
| 2003/0096743 A1 | 5/2003 | Senter et al. | |
| 2003/0109682 A1 | 6/2003 | Santi et al. | |
| 2004/0018194 A1 | 1/2004 | Francisco et al. | |
| 2004/0126379 A1 | 7/2004 | Adolf et al. | |
| 2004/0219155 A1 * | 11/2004 | Thorpe et al. | 424/178.1 |
| 2005/0026971 A1 | 2/2005 | Berger et al. | |
| 2005/0232929 A1 * | 10/2005 | Kadkhodayan et al. | 424/178.1 |

FOREIGN PATENT DOCUMENTS

| | | |
|---|---|---|
| EP | 0088695 A2 | 9/1983 |
| EP | 0 624 377 A2 * | 11/1994 |
| WO | WO 81/01145 A1 | 4/1981 |
| WO | WO 86/01720 A1 | 3/1986 |
| WO | WO 98/13059 A1 | 4/1998 |
| WO | WO 01/24763 A2 | 4/2001 |
| WO | WO 2004/012735 A2 | 2/2004 |
| WO | WO 2004/018000 A2 | 3/2004 |

OTHER PUBLICATIONS

Fasken, et al., A leptomycin B-sensitive Homologue of Human CRM1 Promotes Nuclear Export of Nuclear Export Sequence-containing Proteins in Drosophila Cells, The Journal of Biological Chemistry, 2000, vol. 275, No. 3, pp. 1878-1886.*
Alberts et al., *Molecular Biology of the Cell*, 4th Ed., Garland Science (New York, NY 2002), pp. 739-757.
American Chemical Society, Chemical Substance Reg. No. 87081-35-4, for Leptomycin B.
Carl et al., *J. Med. Chem.* 24 (3), 479-480 (1981), "A Novel Connector Linkage Applicable in Prodrug Design".
Cooper, *The Cell: A Molecular Approach*, ASM Press (Washington DC, 1997), pp. 381-383, 492-500.
Doronina et al., *Nature Biotechnology* 21 (7), 778-784 (2003) (*erratum*, p. 941), "Development of Potent Mono-clonal Antibody Auristatin Conjugates for Cancer Therapy".
Dubowchik et al., *Bioconjugate Chem.* 13, 855-869 (2002), "Cathepsin B-Labile Dipeptide Linkers for Lysosomal Release of Doxorubicin from Internalized Immunoconjugates: Model Studies of Enzymatic Drug Release and Antigen-specific in Vitro Anticancer Activity".
Dubowchik et al., *Bioorg. Med. Chem. Lett.*, 8, 3347-3352 (1998), "Cathepsin B-Sensitive Dipeptide Prodrugs. 2. Models of Anticancer Drugs Paclitaxel (Taxol®), Mitomycin C and Doxorubicin".
Dubowchik et al., *Biorg. Med. Chem. Lett.* 8, 3341-3346 (1998), "Cathepsin B-Sensitive Dipeptide Prodrugs. 1. A Model Study of Structural Requirements for Efficient Release of Doxorubicin".

(Continued)

*Primary Examiner*—Jon P Weber
*Assistant Examiner*—Abdel A Mohamed
(74) *Attorney, Agent, or Firm*—Stephen C. D'Amico

(57) ABSTRACT

A conjugate of an active agent and a targeting moiety having affinity for a target cell, in which the active agent has been modified by attachment of a cell membrane-impermeabilizing group so that, if the active agent so modified is cleaved from the conjugate in the blood plasma instead of inside the target cell, the cell membrane-impermeabilizing group prevents or limits entry of the modified active agent into cells, thus reducing its systemic or non-specific adverse effects, including toxicity.

1 Claim, 5 Drawing Sheets

OTHER PUBLICATIONS

Dubowchik et al., *Pharmacology & Therapeutics*, 83, 67-123 (1999), "Receptor-Mediated and Enzyme-Dependent Targeting of Cytotoxic Cancer Drugs".

Gagliardi et al., *J. Med. Chem.*, 41, 1883-1893 (1998), "Synthesis and Structure-Activity Relationships of Bafilomycin $A_1$ Derivatives as Inhibitors of Vacuolar $H^+$-ATPase".

Garnett, *Adv. Drug Delivery Rev.*, 53, 171-216 (2001), "Targeted drug conjugates: principles and progress".

Isawa et al., *J. Antibiotics* 34 (12), 1587-1590 (1981), "Demethylation of Ansamitocins and Related Compounds".

Kalesse et al., *Synthesis* 2002, 8, 981-1003, "The Chemistry and Biology of the Leptomycin Family".

Kawai et al., *Chem. Pharm. Bull.*, 32 (9), 3441-3451 (1984), "Chemical Modification of Ansamitocins. III. Synthesis and Biological Effects of 3-Acyl Esters of Maytansinol".

King et al., *J. Med. Chem.* 45, 4336-4343 (20020, "Monoclonal Antibody Conjugates of Doxorubicin Prepared with Branced Peptide Linkers: Inhibition of Aggregation by Methoxytriethyleneglycol Chains".

Kupchan et al., *J. Am. Chem. Soc.*, 97, 5294-5295 (1975), "Novel Maytansinoids, Naturally Occurring and Synthetic Antileukemic Esters of Maytansinol".

Kupchan et al., *J. Med. Chem.* 21 (1), 31-37 (1978), "Structural Requirements for Antileukemic Activity among the Naturally Occurring and Semisynthetic Maytan-sinoids".

Mattson et al., *J. Biol. Chem.*, 269 (40), 24979-24982 (1994), "Isolation and Reconstitution of a Vacuolar-type Proton Pump of Osteoclast Membranes".

Riddles et al., *Anal Biochem.*, 94 75-81 (1979), "Ellman's Reagent: 5,5'-Dithiobis(2-nitrobenzoic Acid)—a Reexamination".

Ritchlin et al., *J. Clin. Investig.*, 111 (6), 831-831 (2003), "Mechanisms of TNF-α- and RANKL-mediated Osteo-clastogenesis and Bone Resorption in Psoriatic Arthritis".

Rodan et al., *Science*, 289, 1508-1514 (2000), "Thera-peutic Approaches to Bone Diseases".

Schacht et al., "Macromolecular Carriers for Drug Targeting," in Wermuth, ed., *The Practice of Medicinal Chemistry*, 2nd Ed., pp. 587-600 (Academic Press 2003).

Sekine et al., *J. Am. Chem. Soc.*, 100, 1001-1002 (1978), "Silyl Phosphites. 6. Reactions of Tri(trimethylsilyl) Phosphite with α-Halocarbonyl Compounds".

Senter et al., *Proc. Am. Assoc. Cancer Res.*, 2004, 45, p. 144, abstract No. 623, "Immunoconjugates comprised of drugs with impaired cellular permeability: A new approach to targeted therapy".

Shen et al., *Biochem. Biophys. Res. Commun.* 1981, 102, 1048-1054, "Cis-aconityl Spacer Between Daunomycin and Macromolecular Carriers: a Model of pH-sensitive Linkage Releasing Drug from a Lysosomotropic Conjugate".

Sundquist et al., *Biochem. Biophys. Res. Commun.*, 168 (1), 309-313 (1990), "Inhibition of Osteoclast Proton Transport by Bafilomycin $A_1$ Abolishes Bone Resorption".

Toki et al., *J. Org. Chem.* 2002, 67, 1866-1872, "Protease Mediated Fragmentation of p-Amidobenzyl Ethers: A New Strategy for the Activation of Anticancer Prodrugs".

Trouet et al., *Proc. Natl. Acad. Sci. USA*, 79, 626-629 (1982), "A covalent linkage between daunorubicin and proteins that is stable in serum and reversible by lysosomal hydrolases, as required for a lysosomotropic drug-carrier conjugate; In vitro and in vivo studies".

Vaananen et al., *J. Cell Sci.*, 113, 377-381 (2000), "The Cell Biology of Osteoclast Function".

Yoshimori et al., *J. Biol. Chem.* 266 (26), 17707-17712 (1991), "Bafilomycin $A_1$, a Specific Inhibitor of Vacuolar-type $H^+$-ATPase, Inhibits Acidification and Protein Degradation in Lysosomes of Cultured Cells".

Senter et al. Proc. AACR 45, 144, abst. No. 623 (Mar. 2004), "Immunoconjugates Comprised of Drugs with Impaired Cellular Permeability: A new Approach to Targeted Therapy".

* cited by examiner

Fig. 7

(1) Maytansinol (2) Maytansinol 3-bromoacetate

Reagents: BrCH₂COOH, DCC/EDC, DMAP

*Bacillus megaterium*

(3) 3-Bromoacetyl-20-desmethylmaytansine

P(OSiMe₃)₃

NMe₃

(4) 20-Desmethyl-3-phosphonoacetylmaytansine (5) 3-Trimethylammoniumacetyl-20-desmethylmaytansine

CONJUGATES WITH REDUCED ADVERSE SYSTEMIC EFFECTS

CROSS-REFERENCE TO RELATED APPLICATIONS

This application claims the benefit under 35 U.S.C. § 119(e) of U.S. Provisional Application No. 60/580,142 filed Jun. 15, 2004, the disclosure of which is incorporated herein by reference.

BACKGROUND OF THE INVENTION

1. Field of the Invention

This invention relates to conjugates having reduced adverse systemic effects and methods for making and using the same.

2. Description of Related Art

Chemotherapy involves administering to a patient an active agent designed to modulate one or more cellular functions of a target cell associated with a disease or disorder. The modulating action can range from reducing an activity, such as down-regulating the expression of a gene, to suppressing the activity entirely. Frequently, but not necessarily, the target cell is a cancer cell, in which case the cellular functions modulated are those vital to cell survival, with the objective of affecting them to such an extent that the cell cannot survive and a cytocidal effect is achieved—that is, the active agent is a cytotoxin.

A common drawback of chemotherapy is the effect of the active agent on non-target cells as well as target cells, resulting in systemic (non-selective) adverse effects. In principle this drawback can be overcome by designing an active agent that affects only the target cell, but in practice absolute selectivity is rarely achieved.

An alternative approach is to covalently link the active agent via a linker moiety to a targeting moiety that has affinity for the target cell, forming a targeting moiety/linker moiety/active agent conjugate. The active agent is latently active: in its conjugated form it is inactive, but when released from the conjugate by cleavage of the linker moiety, it is active. The targeting moiety directs the conjugate to the target cell, after which the conjugate is internalized by endocytosis. As an illustration, the targeting moiety can be an antibody (particularly a monoclonal antibody or "mAb") having specific affinity for a tumor-associated antigen ("TAA") characteristic of a target cancer cell and the active agent is an anti-cancer drug. In the vernacular of the art, the active agent is referred to as a "warhead," analogizing the conjugate to a military guided missile.

The linker moiety is designed to be stable outside of the target cell but unstable inside it (or, at least, more stable outside than inside). Cleavage of the linker moiety in response to conditions prevalent inside the target cell releases the active agent. Intracellular conditions triggering cleavage can be varied. The end destination of an endocytosed molecule is normally a lysosome inside the cell. The lysosomal environment is more acidic (typically about pH 5) than blood plasma (typically about pH 7.3), so that a linker moiety that is pH sensitive can be selectively cleaved inside a target cell. Also, a lysosome contains acid hydrolases, which are peptidases active at acidic pH's. A peptidic linker moiety that is a specific substrate for the acid hydrolases will be cleaved preferentially inside a lysosome. Or, a redox-potential sensitive linker moiety may be preferentially cleaved in response to a difference in redox potential.

Nevertheless, a certain amount of premature cleavage of the linker moiety is virtually unavoidable. Applying the rule of thumb of a 10× differential per pH unit in the rate of a first-order acid catalyzed reaction, a pH sensitive linker moiety will cleave in blood serum at about 1% of the lysosomal rate. Or, a peptidic linker moiety designed to be a specific substrate for a lysosomal acid hydrolase may be a non-specific substrate for a serum protease. Whenever premature cleavage occurs, the result is "leakage" of the active agent into the blood plasma and a consequent risk of a negative systemic effect. Such risk is especially serious where the active agent is toxic towards cells generally.

Thus, it is desirable to develop solutions to the problem of premature active agent release in a conjugate resulting in adverse systemic effects.

BRIEF SUMMARY OF THE INVENTION

In a first aspect, this invention provides a conjugate that has affinity for a target cell and releases inside the target a modified active agent that modulates one or more cellular functions of the target cell, having the structure

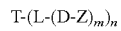
$$T\text{-}(L\text{-}(D\text{-}Z)_m)_n$$

wherein

T is a targeting moiety that has affinity for the target cell;

D-Z is a modified active agent comprising a cell membrane-impermeabilizing moiety Z covalently attached to an active agent D that modulates one or more cellular functions of the target cell when inside the target cell;

L is a linker moiety covalently linking targeting moiety T and modified active agent D-Z, which linker moiety L is preferentially susceptible to cleavage inside the target cell to release modified active agent D-Z;

m is an integer ranging from 1 to 64; and n is an integer ranging from 1 to 12.

In a second aspect, this invention provides a method of making a conjugate that has affinity for a target cell and releases inside the target cell a modified active agent that modulates one or more cellular functions of the target cell, comprising the steps of:

(a) covalently attaching a cell membrane-impermeabilizing moiety Z to an active agent D that modulates one or more cellular functions of the target cell when inside the target cell, to prepare a modified active agent D-Z; and (b) covalently linking active agent D or modified active agent D-Z to a targeting moiety T via a linker moiety L to form a conjugate of the structure

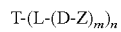
$$T\text{-}(L\text{-}(D\text{-}Z)_m)_n$$

wherein targeting moiety T has affinity for the target cell;

linker moiety L is preferentially susceptible to cleavage inside the target cell to release modified active agent D-Z;

m is an integer ranging from 1 to 64; and n is an integer ranging from 1 to 12.

The linking step (b) can be performed either before or after the attachment of cell membrane-impermeabilizing moiety Z to active agent D.

In a third aspect, this invention provides a method for modulating one or more target cellular functions of a target cell in a subject (e.g., a human or an animal), comprising administering to the subject an effective amount of a conjugate that has affinity for a target cell and releases inside the target cell a modified active agent that modulates one or more cellular functions of the target cell, which conjugate has the structure

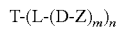

wherein

T is a targeting moiety that has affinity for the target cell;

D-Z is a modified active agent comprising a cell membrane-impermeabilizing moiety Z covalently attached to an active agent D that modulates one or more cellular functions of the target cell when inside the target cell;

L is a linker moiety covalently linking targeting moiety T and modified active agent D-Z, which linker moiety L is preferentially susceptible to cleavage inside the target cell to release modified active agent D-Z;

m is an integer ranging from 1 to 64; and n is an integer ranging from 1 to 12.

In a fourth aspect, this invention provides for the use of a conjugate according to the first aspect for preparation of a medicament for the treatment of a disease of cell proliferation, in particular cancer.

BRIEF DESCRIPTION OF THE DRAWINGS

FIG. 7 shows the synthesis of maytansinoid compounds usable as modified active agents in conjugates of this invention.

DETAILED DESCRIPTION OF THE INVENTION

Figure 1:
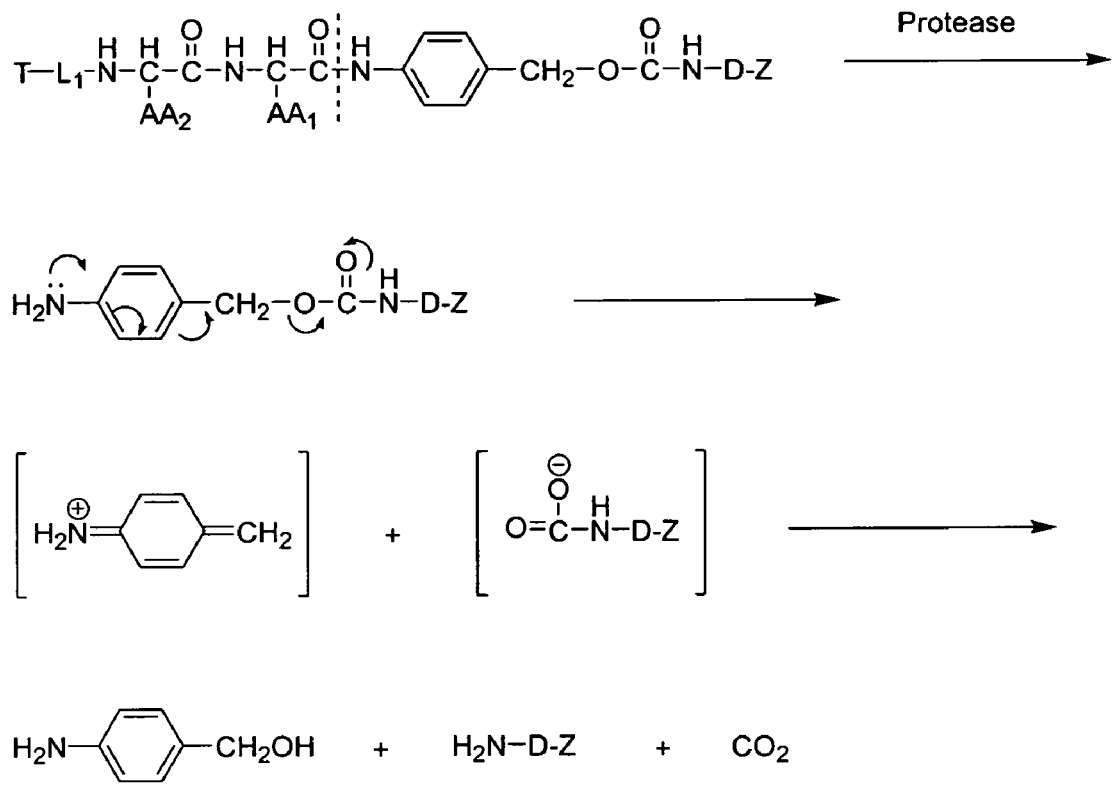
FIG. 1 shows the chemistry underlying a protease-cleavable self-immolating linker moiety.

The role of the targeting moiety is to direct the conjugate to the target cell, via its affinity for a cognate site on the surface of the target cell. Preferred targeting moieties T include antibodies, growth factors, serum proteins, polysaccharides or synthetic polymers, especially those that are ligands for cell-surface receptors or antigens. Preferably, the cell-surface receptor or antigen is unique to the target cell or at least present in a greater amount there than in a non-target cell. As the cognate ligand of such cell-surface receptor or antigen, targeting moiety T preferentially binds to a target cell compared to a non-target cell, which is what is meant by the statement that targeting moiety T has an affinity for a target cell. Monoclonal antibodies are especially preferred. General protocols for the design and use of conjugated antibodies are described in Monoclonal Antibody-Based Therapy of Cancer, Vol. 15, Michael L. Grossbard, ed. (Marcel Dekker 1998) (incorporated herein by reference).

The discovery of molecular markers, or tumor-associated antigens (TAAs), has opened the possibility of using antibodies as targeting moieties. Among the TAAs that may be targeted by antibodies are the carcinoembryonic antigen (CEA), associated with gastro-intestinal tract and some lung and breast tumors; α-fetoprotein; gangliosides such as L6 Ag; blood group carbohydrates such as Lewis y (Ley); the transferrin receptor; the adenocarcinoma KS1/4; mucins; glycosphingolipids; selecting; integrins; other adhesion molecules; mutated forms of tumor suppressor p53; and heat shock proteins overexpressed in tumor cells.

In a preferred embodiment, the antibody is directed against a cellular receptor protein or antigen. Preferred examples include but are not limited to antibodies directed against HER2/neu, epidermal growth factor receptor (EGFR), ErbB2, platelet-derived growth factor (PDGF) receptor, vascular endothelial growth factor receptor 2 (VEGFR2 or KDR), and insulin-like growth factor receptor (IGFR). In other preferred embodiments, the antibody is directed against other clinically relevant tumor markers, including but not limited to polymorphic epithelial mucin (MUC-1), the ovarian cancer-associated antigen CA125, or against the CD33 myeloid-differentiation antigen.

Examples of antibodies that can be used include alemtuzumab, abciximab, biciromab (REOPRO®), infliximab (REMICADE®), 111In-capromab pendetide; trastuzumab (HERCEPTIN®), rituximab (RITUXAN®), CEA-Scan, sulesomab, palivizumab (SYNAGIS®), basiliximab (SIMULECT®), daclizumab (ZENAPAX®), tositumomab, efalizumab, 99mTc-fanolesomab, omalizumab, BR96, eculizumab, MH-1, ATM-027, SC-1, bivatuzumab, BMS-188667, BMS-224818, SGN-15, CAT-213, J-695, metelimumab, CAL, MRA, MLN-2704, OncoRad PR356, licilimomab, MAb-81C6, clenoliximab, Melimmune, HumaRAD16.88, KW-2871, MLN-02, MDX-210, MDX-37, MDX-H210, 3F8, EMD-72000, SS (dsFv)PE38, Oncolym, CaroRx, apolizumab, fontolizumab, Nuvion, SMART anti-L-selectin Mab, TMA-15, YM-337, M60.1, WX-G250, VITAXIN®, mepolizumab, pascolizumab, TNX-901, 5-D12, TheraCIM-h-R3, TriAb, TRX-4, TriGem, HRS-3/A9, BTI-322, siplizumab, Mycograb, 1NG-1(heMAb), HepeX-B, pexelizumab, orgovomab, natalizumab, bevacizumab, cetuximab, epratuzumab, afelimomab, MDX-RA, inolimomab, lintuzumab, CeaVac, mPA7, and mhoe-4.

In another preferred embodiment, the targeting moiety T is a cellular growth factor. Preferred examples of such growth factors include but are not limited to epidermal growth factor (EGF), insulin-like growth factor (ILGF), vascular endothelial growth factor (VEGF), and platelet-derived growth factor (PDGF).

In yet another embodiment, targeting moiety T is a polysaccharide ligand for a cellular receptor. Preferred embodiments include but are not limited to ligands for the selectin receptors, such as Lewis-x, and ligands for growth factor receptors. Examples of polysaccharide ligands that are ligands for growth factor receptors are described in Magnani et al., U.S. Pat. Nos. 6,281,202 and 6,008,203, both incorporated herein by reference.

Targeting moiety T can also be a protein substantially smaller in size than an antibody, for example a protein having a molecular weight of less than about 5,000 Daltons, as described in Briesewitz et al., U.S. Pat. No. 6,372,712 B1 (2002), the disclosure of which is incorporated by reference.

After the targeting moiety has directed the conjugate to the target cell, it may be internalized by endocytosis. For more background information on endocytosis, see, e.g., Cooper, The Cell: A Molecular Approach, ASM Press (Washington D.C., 1997), pp. 381-383, 492-500; and Alberts et al., Molecular Biology of the Cell, 4th Ed., Garland Science (New York, N.Y. 2002), pp. 739-757; the disclosures of which are incorporated herein by reference. In endocytosis, the cell membrane invaginates and progressively occludes a volume of extracellular fluid, culminating in the invaginated section of the cell membrane pinching off as an endocytic vesicle (also referred to as a pinocytic vesicle) inside the cell, thus internalizing the occluded fluid and any molecules dissolved therein. The efficiency of internalization of some materials may be enhanced by the intervention of cognate binding sites (cell-surface receptors, antigens, etc.) for the material, in a process referred to as receptor-mediated endocytosis. The binding sites or receptors for an extracellular ligand accumulate at clathrin-coated pits on the cell membrane, which pits are also starting loci for invagination and endocytosis. The ligands bind to the binding sites and are thus internalized at an enriched concentration, without the need for the cell to take in a correspondingly large volume of extracellular fluid. This process efficiently and selectively internalizes ligands that may be present in only minute concentrations in the extracellular fluid. Alternative endocytosis pathways that do not rely on clathrin exist, such as caveolae-mediated endocytosis and macropynocytosis, but their mechanisms of action are less well understood. When a conjugate according to this invention is internalized by endocytosis, it makes its way to other intracellular vesicular bodies, such as early endosomes, late endosomes, and lysosomes, via a series of fusions and buddings. Cleavage of the linker moiety in response to a prevailing condition inside the one of the vesicular bodies releases modified active agent D-Z. For example, lysosomal fluid is acidic and contains a variety of acid hydrolases and is thus a desirable medium for the cleavage of pH-sensitive or enzymatically sensitive linker moieties.

Active agent D can be a cytotoxin used for cancer chemotherapy. Exemplary cytotoxins include alkylating agents, angiogenesis inhibitors, antimetabolites, DNA cleavers, DNA crosslinkers, DNA intercalators, DNA minor groove binders, enediynes, heat shock protein 90 inhibitors, histone deacetylase inhibitors, microtubule stabilizers, nucleoside (purine or pyrimidine) analogs, nuclear export inhibitors, proteasome inhibitors, topoisomerase (I or II) inhibitors, tyrosine kinase inhibitors. Specific anti-cancer or cytotoxic agents include β-lapachone, ansamitocin P3, auristatin, bicalutamide, bleomycin, bortezomib, busulfan, calicheamycin, callistatin A, camptothecin, capecitabine, CC-1065, cisplatin, cryptophycins, daunorubicin, discodermolide, disorazole, docetaxel, doxorubicin, duocarmycin, dynemycin A, epothilones, etoposide, floxuridine, floxuridine, fludarabine, fluoruracil, gefitinib, geldanamycin, 17-allylamino-17-demethoxygeldanamycin (17-AAG), 17-(2-dimethylaminoethyl)amino 17-demethoxygeldanamycin (17-DMAG), gemcitabine, hydroxyurea, imatinib, interferons, interleukins, irinotecan, leptomycin B, maytansine, methotrexate, mitomycin C, oxaliplatin, paclitaxel, spongistatins, suberoylanilide hydroxamic acid (SAHA), thiotepa, topotecan, trichostatin A, vinblastine, vincristine, and vindesine. As used here, the collective term "maytansinoids" is used to refer to the family of structurally related compounds including maytansine and ansamitocin P3. Preferably, active agent D is selected from the group consisting of maytansinoids and leptomycin B.

While often the cellular functions of the target cell that are modulated are those vital to cell survival, with the objective of impacting them to a degree that the cell cannot survive—i.e., a cytocidal effect is the objective—this is not always necessarily so. For instance, the objective may be to down-regulate an overexpressed gene or partially inhibit an enzymatic activity, without killing the target cell. In other instances, it may be desired to inhibit cell growth or division.

The modification of active agent D by covalent attachment thereto of a cell-impermeabilizing moiety Z imparts a "fail-safe" feature to conjugates of this invention. If for some reason the conjugate should cleave prematurely in the blood plasma and release free modified active agent D-Z, the risk of systemic toxicity or other adverse effect is reduced because cell membrane-impermeabilizing moiety Z prevents transmembrane entry of modified active agent D-Z into the cytosol of a cell. When it is said herein that Z is a cell membrane-impermeabilizing moiety, it is meant that Z renders modified active agent D-Z substantially less capable of permeating across the cell membrane than unmodified active agent D-Z, preferably at least 10 times less permeable, more preferably at least 100 times more permeable. The relative cytotoxicities of the unmodified and modified active agent is possibly an indirect indication of relative permeabilities.

Suitable types of cell membrane-impermeabilizing moiety Z are diverse; it can be cationic, anionic, zwitterionic, or charge-neutral. Exemplary suitable cationic moieties Z are basic groups that are substantially protonated at physiological pH, such as primary, secondary, and tertiary alkyl amine groups, quaternary alkyl or alkylaryl ammonium groups, guanidinium groups, imidazolium groups, triazolium groups, tetrazolium groups, and the like. Exemplary suitable anionic moieties Z are acidic groups that are substantially ionized to their conjugate base form at physiological pH, such as sulfonates, phosphonates, and, in some instances, carboxylates. Zwitterionic moieties Z include moieties that have a carboxylate and an ammonium group. Neutral moieties Z include glucuronate.

Linker moiety L can be a pH sensitive one. While the pH of blood is typically about 7.3 to 7.4, the pH in an endosome is 5.0 to 6.5, and the pH in a lysosome is about 4.0 or even as low as 3.8 during early stages of digestion. The intracellular environment inside tumor tissue has been measured to be 0.5 to 1.0 pH units lower than in normal tissue as well. This pH differential can be exploited to provide a conjugate whose linker is stable until it reaches the lower pH environment of an intracellular compartment. Such a linker can comprise a bond that is stable at neutral pH but is readily cleavable under conditions of low pH, e.g., one stable at a pH between 7 and 8 but readily cleavable at a pH between 4 and 6. Examples of such linkers are cis-aconityl amides and acyl hydrazones, as described in Shen et al., U.S. Pat. No. 4,631,190; U.S. Pat. No. 5,144,011; and *Biochem. Biophys. Res. Commun.* 102, 1048-1054 (1981), the disclosures of which are incorporated herein by reference.

Another preferred type of linker moiety L is a redox-potential sensitive one, such as an alkul-alkyl or alkyl-aryl mixed disulfide wherein the aryl moiety is substituted so as to control the steric and electronic properties of the disulfide towards reaction with thiols. Such a linker provides a means of attenuating the rate of thiol-disulfide interchange such that the linkage is stable in an environment of low reductive potential, e.g., in the extracellular environment having low thiol or glutathione concentration, but is cleaved in conditions of high reduction potential (e.g., an intracellular environment having high thiol or glutathione concentration).

Yet another preferred type of linker L comprises a moiety that is readily cleaved in the presence of an enzyme, such as a peptide sequence that is a recognition sequence for an endosomal or lysosomal peptidase (e.g., a cathepsin, especially cathepsin B or D), with the result that the enzyme recognizes and cleaves the linker at or adjacent to the recognition sequence.

Yet another preferred type of linker L is one having a bond that is readily cleaved upon exposure to radiation, for example a 2-nitrobenzyl ether cleavable upon exposure to light.

A preferred type of linker moiety L is a self-immolating linker. Generally, self-immolating linker moieties comprise a peptide segment that is a substrate (preferably, a specific substrate) for a protease found inside the target cell and a self-immolating segment that "unzips" or decomposes when the peptide segment is cleaved by the protease, releasing the drug moiety D-Z. Preferably, the self-immolating segment comprises a p-aminobenzyl-oxycarbonyl (PABC) group, which can unzip as illustrated in FIG. 1. See Carl et al., *J. Med. Chem.* 24 (3), 479-480 (1981), "A Novel Connector Linkage Applicable in Prodrug Design"; and Carl et al., WO 81/01145 (1981); the disclosures of which are incorporated herein by reference.

In FIG. 1 linker moiety L comprises a PABC group, a dipeptide residue, and a residue $L_1$ forming the balance of the linker L moiety. In this particular instance, modified active agent D-Z has an amino group via which it is attached to linker moiety L. The PABC group serves as a spacer, to prevent modified active agent D-Z from sterically or electronically interfering with cleavage of the dipeptide residue by the protease. The dipeptide residue has amino acid side chain groups $AA_1$ and $AA_2$, which make it a specific substrate for the protease. After cleavage of the dipeptide by the protease as indicated by the dotted line, the PABC group "unzips" in a 1,6-fragmentation reaction to release free modified active agent, in the form of its free amine $H_2N$-D-Z.

The linkage site of drug moiety $H_2N$-D-Z in FIG. 1 is an amino group, which in turn is connected to the PABC group, forming a carbamate linkage. Alternatively the linkage site of the drug moiety can be a hydroxyl group, as in HO-D-Z, with the corresponding conjugate having the structure shown below and the self-immolation chemistry proceeding generally analogously in a 1,6-fragmentation reaction upon cleavage of the dipeptide residue. See Toki et al., *J. Org. Chem.* 67, 1866-1872 (2002), the disclosure of which is incorporated herein by reference.

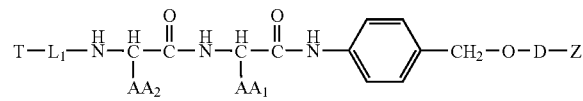

Where linker moiety L is designed to be cleaved by a protease, the protease is preferably a lysosomal acid hydrolase, especially cathepsin B. Cathepsin B preferentially cleaves peptides where $AA_1$ is a basic or strongly hydrogen bonding amino acid residue (as in lysine, arginine, or citrulline) and $AA_2$ is a hydrophobic residue (as in phenylalanine, valine, alanine, leucine, or isoleucine). See Dubowchik et al., *Biorg. Med. Chem. Lett.* 8, 3341-3346 (1998), "Cathepsin B-Sensitive Dipeptide Prodrugs. 1. A Model Study of Structural Requirements for Efficient Release of Doxorubicin"; Dubowchik et al., *Bioorg. Med. Chem. Lett.,* 8 3347-3352 (1998), "Cathepsin B-Sensitive Dipeptide Prodrugs. 2. Models of Anticancer Drugs Paclitaxel (TAXOL®), Mitomycin C and Doxorubicin"; and Dubowchik et al., *Bioconjugate Chem.* 13, 855-869 (2002), "Cathepsin B-Labile Dipeptide Linkers for Lysosomal Release of Doxorubicin from Internalized Immunoconjugates: Model Studies of Enzymatic Drug Release and Antigen-specific in Vitro Anticancer Activity"; the disclosures of which are incorporated by reference.

Other disclosures relating to the general principles of self-immolating linker moieties and specific examples thereof include: Dubowchik et al., Pharmacology & Therapeutics, 83, 67-123 (1999), "Receptor-Mediated and Enzyme-Dependent Targeting of Cytotoxic Cancer Drugs"; Firestone et al., U.S. Pat. No. 6,214,345 B1 (2001); Toki et al., *J. Org. Chem.* 67, 1866-1872 (2002), "Protease-Mediated Fragmentation of p-Amidobenzyl Ethers: A New Strategy for the Activation of Anticancer Prodrugs"; Doronina et al., *Nature Biotechnology* 21 (7), 778-784 (2003) (erratum, p. 941), "Development of Potent Monoclonal Antibody Auristatin Conjugates for Cancer Therapy"; and Senter et al., US 2003/096743 A1 (2003); the disclosures of which are incorporated by reference.

Thus, a preferred linker moiety L comprises the structure

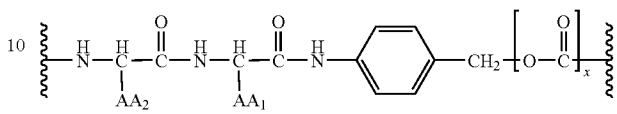

wherein x is 0 or 1, $AA_1$ is a lysine, arginine, or citrulline amino acid side chain residue and $AA_2$ is a phenylalanine, valine, alanine, leucine, or isoleucine amino acid side chain residue.

Figure 2:
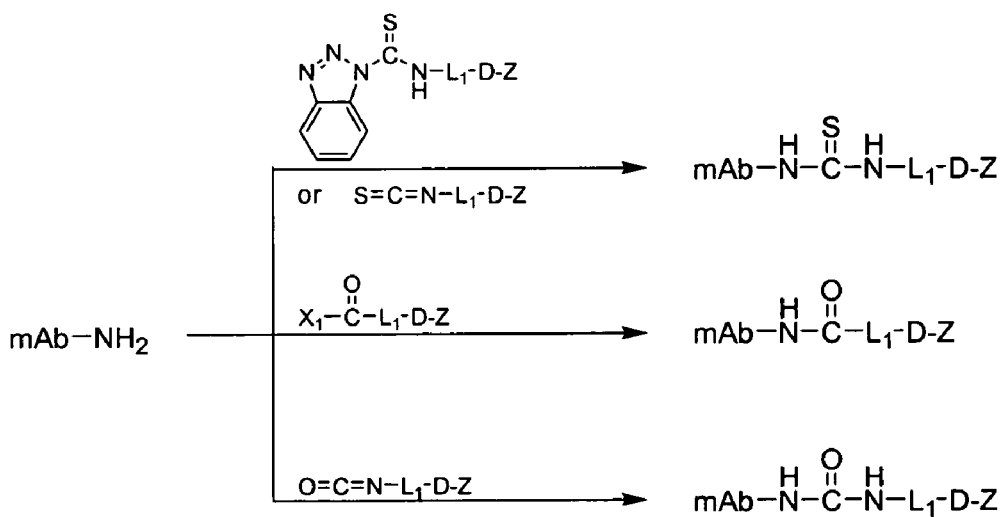
FIGS. 2 through 4 show schemes for the assembly of conjugates of this invention.

A linker moiety L is preferentially cleaved inside a target cell if its cleavage rate inside thereof is substantially greater than in blood plasma. Preferably, the cleavage rate inside the target cell is at least 10×, more preferably at least 100× greater than in blood plasma.

Where targeting moiety T is an antibody (preferably a monoclonal antibody, or mAb), a preferred site for bonding a linker moiety L is an ϵ-amino groups of a lysine residue (lysine residues are found throughout the light and heavy chains of the antibody). Linkage of targeting moiety T and linker moiety L can be effected via an amide link by reaction with an activated acyl group, via an urea link by reaction with an isocyanate group, or via a thiourea link by reaction with a thioisocyanate group or a thioisocyanate equivalent, as shown in FIG. 2. (In FIG. 2 and the other figures, $L_1$ has the same meaning as ascribed previously, i.e., a generalized representation of the balance of linker moiety L remaining outside of the atoms or groups thereof specifically depicted. $X_1$ is a leaving group such as OH, O—N-succinimide, O-4-nitrophenyl, O-penta- or O-tetrafluorophenyl, F, Cl, Br, I, and the like.)

Figure 3:
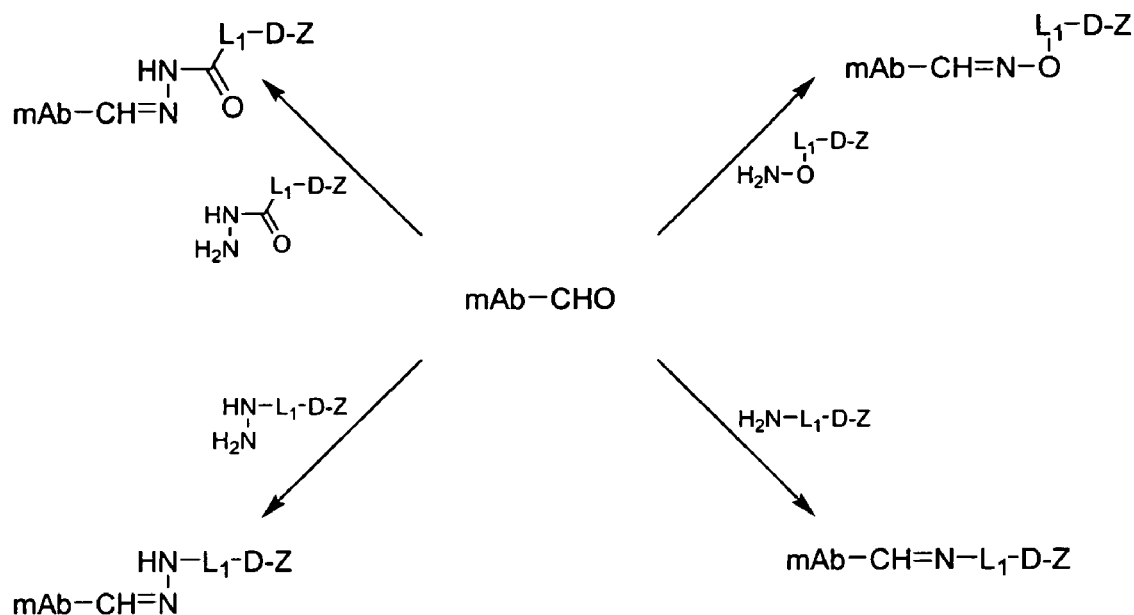

Another bonding site on targeting moiety T is a sugar residue in the hinge region of the antibody, its location away from the antibody binding site making it an attractive bonding site. For instance, the sugars can be oxidized (e.g., with periodate) to provide aldehyde groups that can then be used in coupling reactions, via imine groups, hydrazone or hydrazone-equivalent groups, or oximino groups, as shown in FIG. 3.

Figure 4:
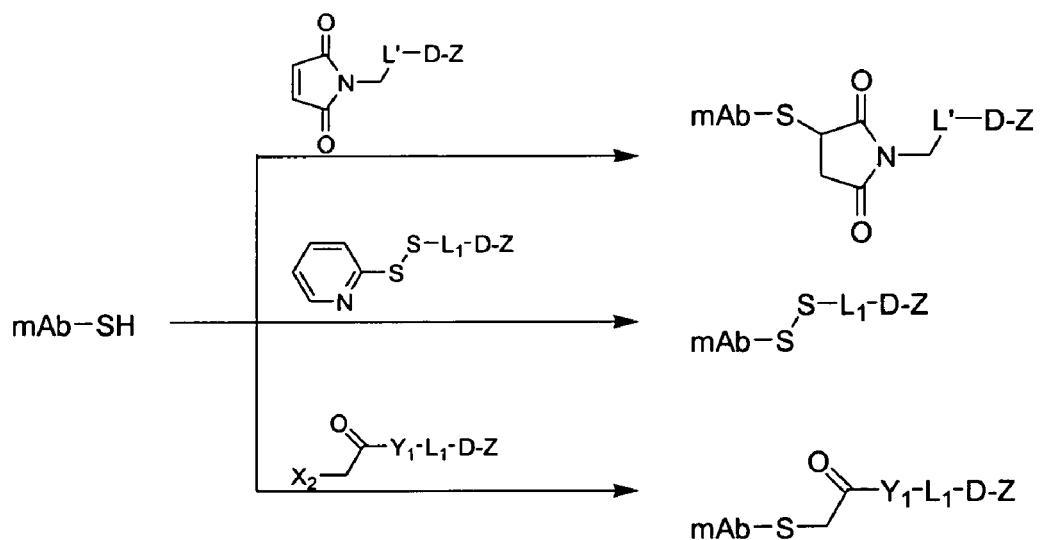

A third binding site for targeting moiety T is as thiol group, by addition across a maleimide group, by displacement of a substituent alpha to a carbonyl group, or formation of a disulfide with a thiol group in the linker in a disulfide exchange reaction, as shown in FIG. 4. (In the figure, $X_2$ is a nucleophilically displaceable group such as $OSO_2$(alkyl), Cl, Br, I, and the like and $Y_1$ is a divalent moiety such as $CH_2$, O, NH, N(alkyl), and the like.

Those skilled in the art will also appreciate that a broad range of other linker moieties can be used in the conjugates of this invention. Additional disclosures relating to linker moieties that can be used include: Senter et al., U.S. Pat. No. 4,952,394 (1990); Kaneko et al., U.S. Pat. No. 5,137,877 (1992); Chari et al., U.S. Pat. No. 5,416,064 (1995); Willner et al., U.S. Pat. No. 5,708,146 (1998); King et al., U.S. Pat. No. 5,824,805 (1998); Chari et al., U.S. Pat. No. 5,846,545 (1998); Hellstrom et al., U.S. Pat. No. 5,869,045 (1999); Hellstrom et al., U.S. Pat. No. 5,980,896 (1999); Chari et al., U.S. Pat. No. 6,333,410 B1 (2001); Chari et al., U.S. Pat. No.

6,436,931 B1 (2002); Chari et al., U.S. Pat. No. 6,441,163 B1 (2002); Chari et al., US 2003/0055226 A1 (2003); Firestone, WO 98/13059 (1998); King et al., U.S. Pat. No. 6,759,509 (2004); Chari, WO 01/24763 A2 (2001); Franciso et al., US 2004/0018194 A1 (2004); Berger et al., US 2005/0026971 A1 (2005); Adolf et al., US 2004/0127379 A1 (2004); and Garnett, *Adv. Drug Delivery Reviews* 53, 171-216 (2001), "Targeted Drug Conjugates: Principles and Progress."

Assembly of a conjugate of this invention can be effected either by covalently linking together targeting moiety T and linker moiety L, followed by covalent attachment of active agent D-Z. Alternatively, the order of the steps can be reversed, with the linker moiety L-active agent D-Z attachment formed first. In yet another embodiment, a conjugated moiety T-L-(D)$_n$ is formed first, and then cell membrane impermeabilizing group Z is attached to D. Or, active agent D can be covalently linked to linker moiety L before cell membrane-impermeabilizing group Z is attached thereto. For the attachment of more than one modified active agent D-Z to each linker moiety L (i.e., m>1), a linker moiety L comprising a dendrimer can be used.

Structures of illustrative conjugates according to this invention are shown in formulae I through XII:

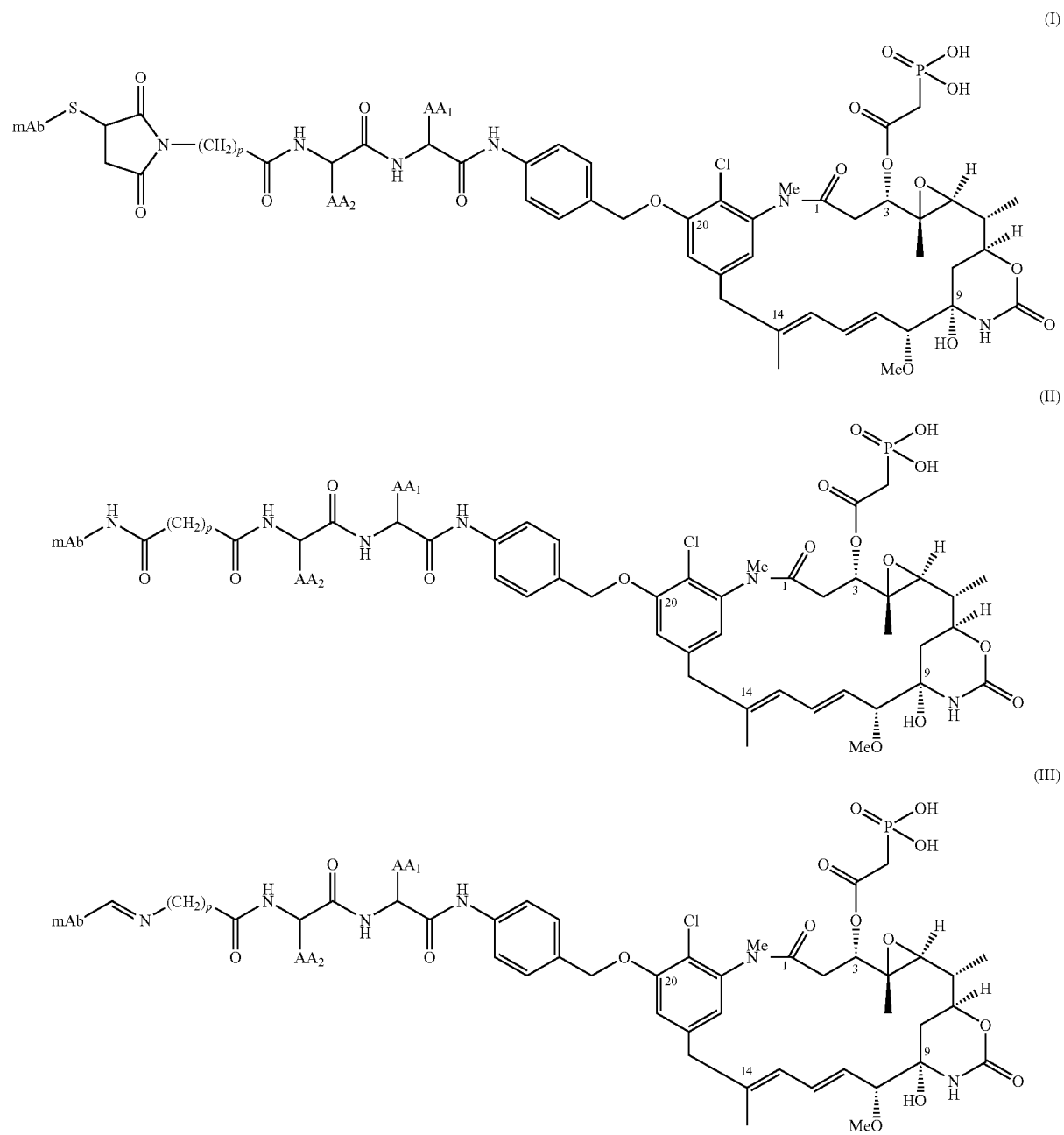

-continued
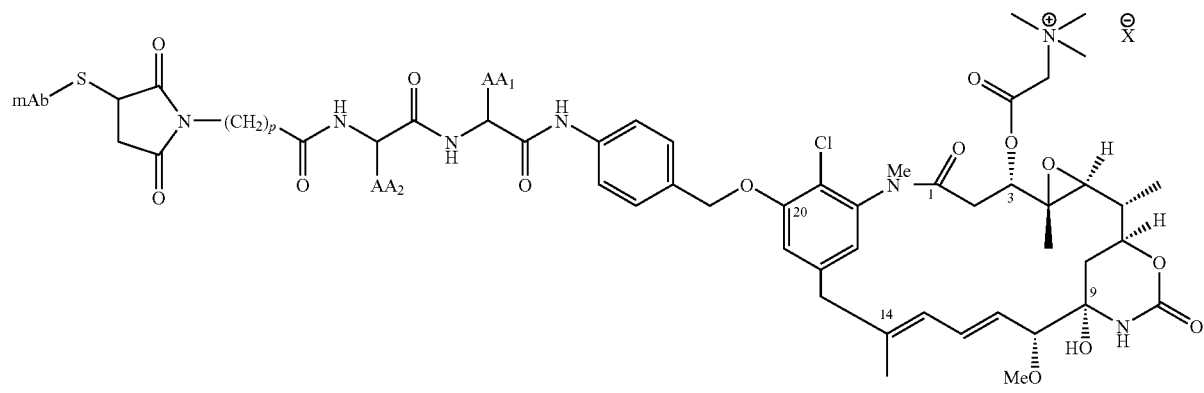
(IV)
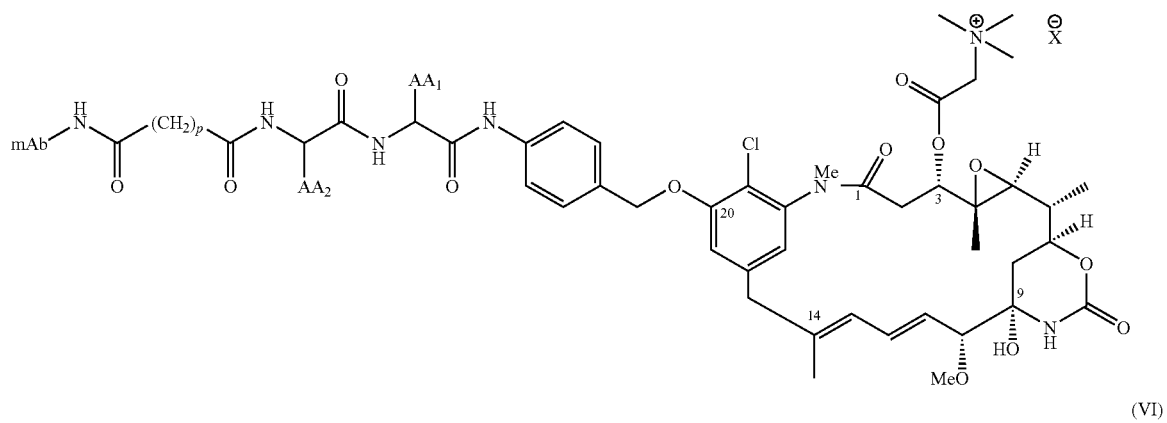
(V)
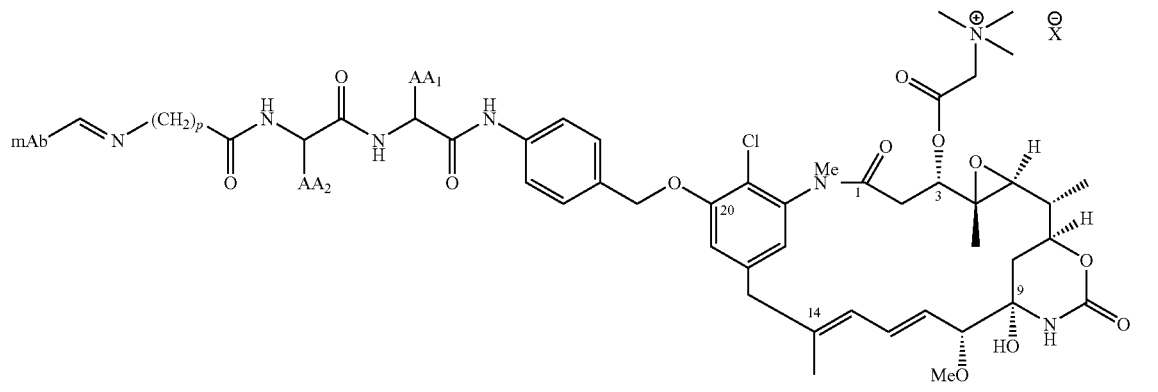
(VI)
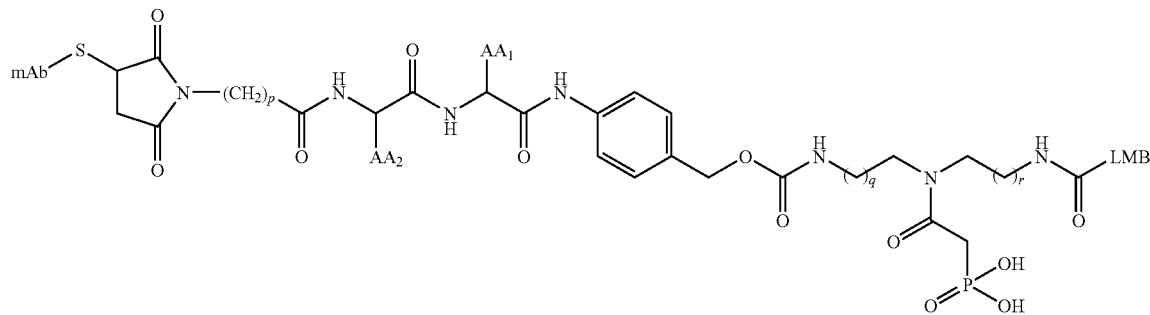
(VII)

-continued
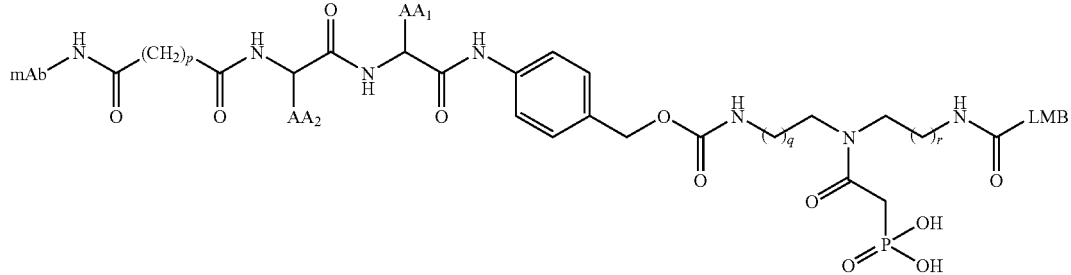
(VIII)
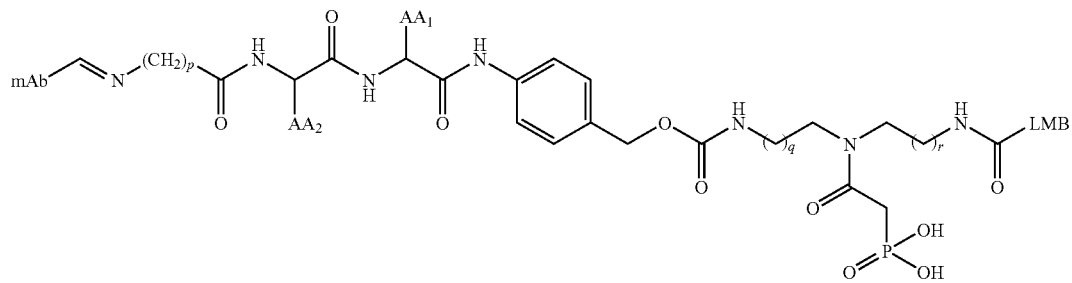
(IX)
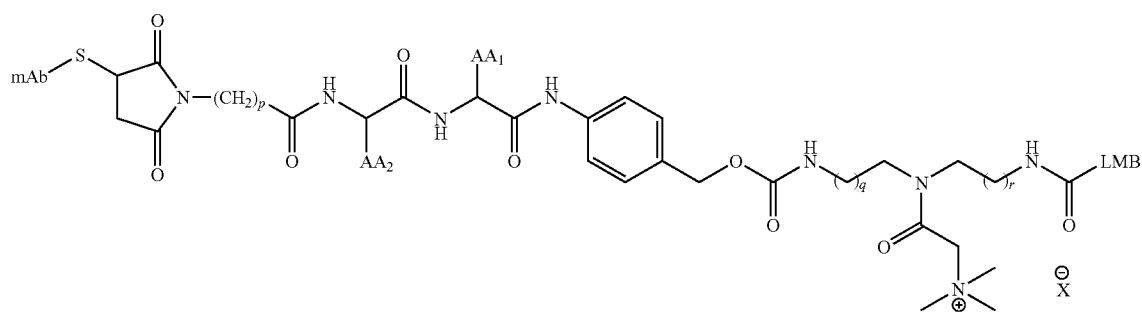
(X)
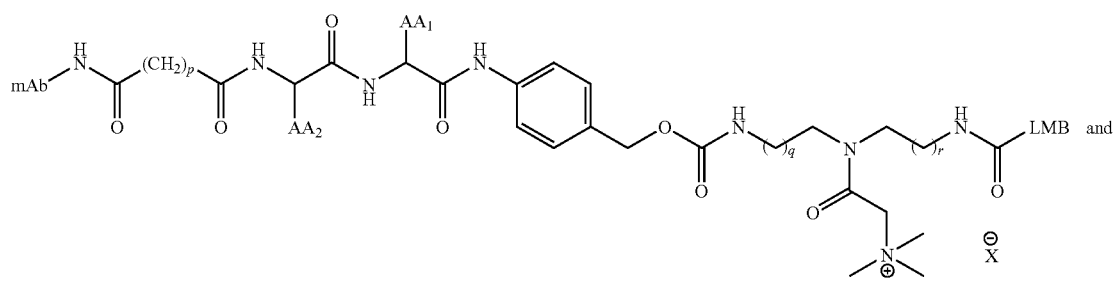
(XI)
and
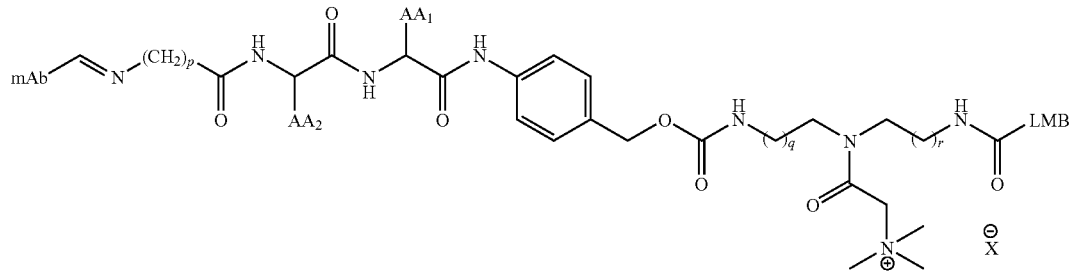
(XII)
In the foregoing formulae I-XII:
  mAb is a monoclonal antibody;
  L in formulae XIII and XIV is a linker moiety as defined hereinabove;
  $AA_1$ is a lysine, arginine, or citrulline amino acid side chain residue;
  $AA_2$ is a phenylalanine, valine, alanine, leucine, or isoleucine amino acid side chain residue;

p in formulae I to XII is an integer from 1 to 6;
q in formulae VII to XII is an integer from 1 to 5;
r in formulae VII to XII is an integer from 1 to 5;
—C(=O)LMB in formulae VII to XII is a leptomycin B residue, having the structure

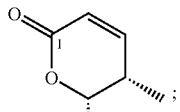
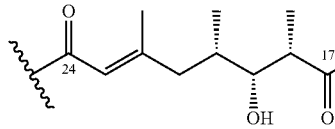

and $X^{\ominus}$ in formulae IV to VI and X to XII is a pharmaceutically acceptable counteranion (chloride, acetate, citrate, fumarate, maleate, succinate, benzoate, sulfate, tartrate, and the like).

Where a range is stated in this specification, as in connection with subscripts p, q, and r above, such range includes the end points of the range.

Conjugates I to VI have a maytansinoid (an anti-cancer cytotoxin) compound as the active agent D. Linkage to the targeting moiety mAb is variously via maleimide, amide, or imine linkages as shown. The cell membrane-impermeabilizing moiety Z is anionic (phosphonate, conjugates I to III) or cationic (quaternary ammonium; conjugates IV to VI). The linker moiety includes a self-immolating moiety and a protease susceptible dipeptide moiety.

Conjugates VII to XII have leptomycin B (a cytotoxin that acts as a nuclear export inhibitor) as the active agent D. Linkage to the targeting moiety mAb is variously via maleimide, amide, or imine linkages as shown. The cell membrane-impermeabilizing moiety Z is anionic (phosphonate, conjugates VII to IX) or cationic (quaternary ammonium; conjugates X to XII). The linker moiety includes a self-immolating moiety and a protease susceptible dipeptide moiety.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by the present invention. Polymorphic crystalline forms and solvates are also encompassed within the scope of this invention.

Diseases treatable by conjugates of this invention include, but are not limited to, hyperproliferative diseases, including: cancers of the head and neck which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; treat ovarian cancer; small cell and non-small cell lung cancer; breast cancer sarcomas, such as fibrosarcoma, malignant fibrous histiocytoma, embryonal rhabdomysocarcoma, leiomysosarcoma, neurofibrosarcoma, osteosarcoma, synovial sarcoma, liposarcoma, and alveolar soft part sarcoma; neoplasms of the central nervous systems, particularly brain cancer; lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma.

Clinically, practice of the methods and use of conjugates described herein will result in a reduction in the size or number of the cancerous growth and/or a reduction in associated symptoms (where applicable). Pathologically, practice of the method and use of conjugates described herein will produce a pathologically relevant response, such as: inhibition of cancer cell proliferation, reduction in the size of the cancer or tumor, prevention of further metastasis, and inhibition of tumor angiogenesis.

In another aspect of the present invention, non-cancer disorders that are characterized by cellular hyperproliferation are treated. Illustrative examples of such disorders include but are not limited to: atrophic gastritis, inflammatory hemolytic anemia, graft rejection, inflammatory neutropenia, bullous pemphigoid, coeliac disease, demyelinating neuropathies, dermatomyositis, inflammatory bowel disease (ulcerative colitis and Crohn's disease), multiple sclerosis, myocarditis, myositis, nasal polyps, chronic sinusitis, pemphigus vulgaris, primary glomerulonephritis, psoriasis, surgical adhesions, stenosis or restenosis, scleritis, scleroderma, eczema (including atopic dermatitis. irritant dermatitis, allergic dermatitis), periodontal disease (i.e., periodontitis), polycystic kidney disease, and type I diabetes. Other examples include vasculitis (e.g., Giant cell arteritis (temporal arteritis, Takayasu's arteritis), polyarteritis nodosa, allergic angiitis and granulomatosis (Churg-Strauss disease), polyangitis overlap syndrome, hypersensitivity vasculitis (Henoch-Schonlein purpura), serum sickness, drug-induced vasculitis, infectious vasculitis, neoplastic vasculitis, vasculitis associated with connective tissue disorders, vasculitis associated with congenital deficiencies of the complement system, Wegener's granulomatosis, Kawasaki's disease, vasculitis of the central nervous system, Buerger's disease and systemic sclerosis); gastrointestinal tract diseases (e.g., pancreatitis, Crohn's disease, ulcerative colitis, ulcerative proctitis, primary sclerosing cholangitis, benign strictures of any cause including ideopathic (e.g., strictures of bile ducts, esophagus, duodenum, small bowel or colon); respiratory tract diseases (e.g., asthma, hypersensitivity pneumonitis, asbestosis, silicosis and other forms of pneumoconiosis, chronic bronchitis and chronic obstructive airway disease); nasolacrimal duct diseases (e.g., strictures of all causes including ideopathic); and eustachean tube diseases (e.g., strictures of all causes including ideopathic).

Another disease that can be treated by conjugates of this invention is osteoporosis. Bone matrix is a material in a continuous state of remodeling, with specialized cells (osteoblasts) continuously depositing bone matrix and other specialized cells (osteoclasts) continuously eroding it. In a subject suffering from osteoporosis, bone matrix is eroded faster by the osteoclasts than it is deposited by the osteoblasts, leading to a net loss of bone matrix. Osteoclast-mediated bone erosion proceeds via the secretion of acid onto the bone surface by vacuolar $H^+$-ATPase located in the osteoclast membrane.

Bafilomycin $A_1$ is a macrolide cytotoxin that was originally identified as an antibacterial and antifungal agent (Hagenmaier et al., U.S. Pat. No. 4,558,139 (1985)) but has since been shown to be also a potent and specific inhibitor of vacuolar $H^+$-ATPase. The bone resorption process can be blocked by inhibition of osteoclastic vacuolar $H^+$-ATPase by bafilomycin $A_1$. Sundquist et al., *Biochem. Biophys. Res. Commun.*, 168 (1), 309-313 (1990); Mattsson et al., *J. Biol. Chem.* 269 (40), 24979-24982 (1994).

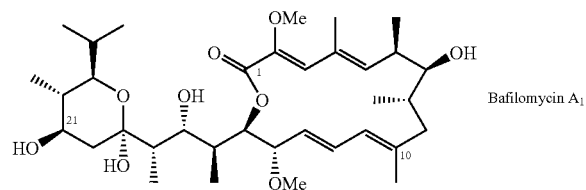

Bafilomycin $A_1$

Thus, conjugates according to this invention where the active agent D is bafilomycin $A_1$ or a related compound (collectively "bafilomycene compounds"), as disclosed in Herslöf et al., U.S. Pat. No. 5,354,773 (1994), incorporated herein by reference, can be used to treat osteoporosis.

Figure 5:
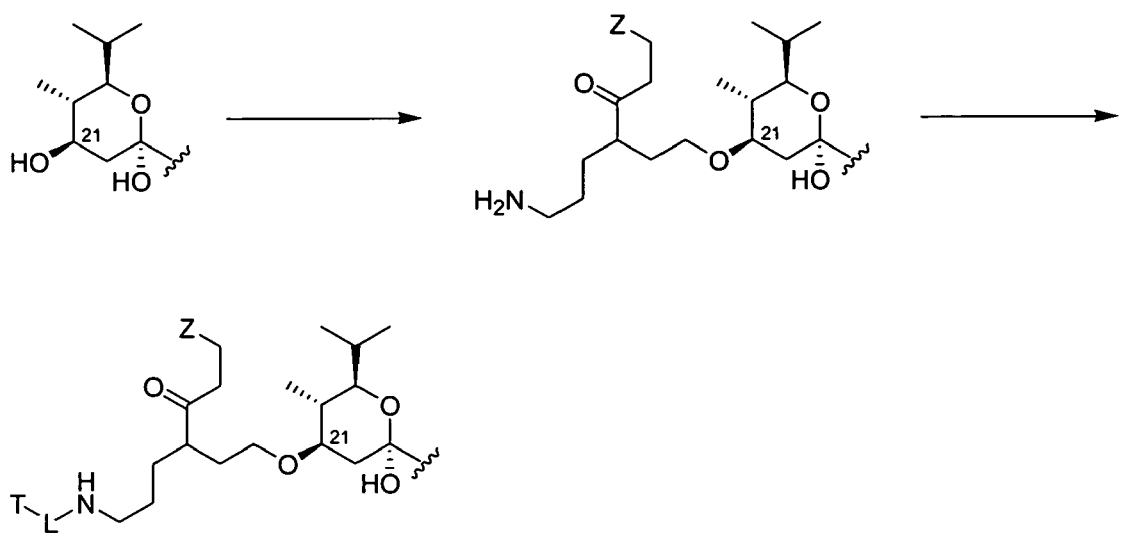
FIGS. 5 and 6 show schemes for the attachment of targeting moieties to bafilomycin modified active agents.

Position 21 of bafilomycin $A_1$ is a suitable position both for modification of bafilomycin $A_1$ with a cell membrane-impermeabilizing group Z and for attachment to a linker moiety L (and, via linker moiety L, a targeting moiety T). Using the procedure of Gagliardi et al., *J. Med. Chem.* 41, 1883-1893 (1998), the disclosure of which is incorporated herein by reference, bafilomycin can be so modified and attached as shown in FIG. 5 (bafilomycin $A_1$ shown only as a partial structure for conciseness).

Figure 6:
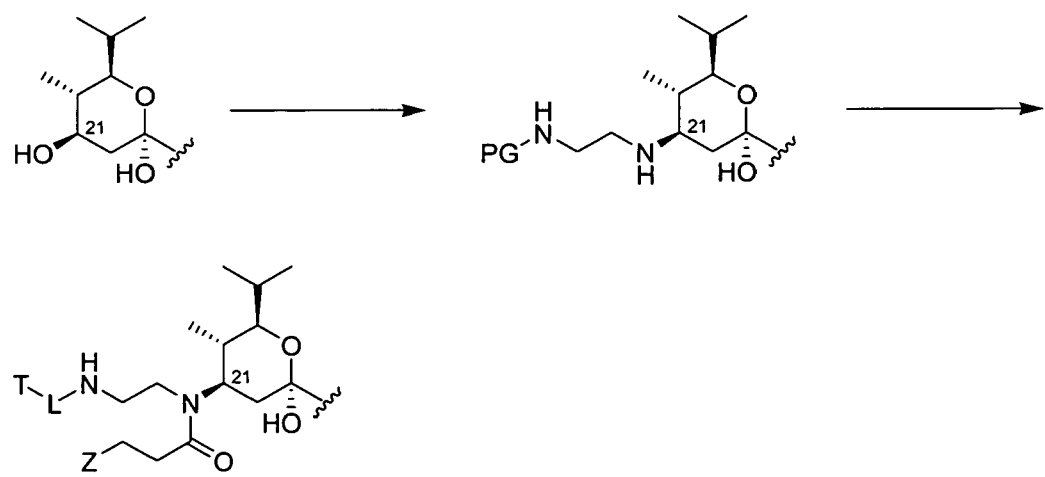

Alternative modification/attachment chemistry is shown in FIG. 6, in which the $C_{21}$ oxygen is not retained but is instead replaced by a nitrogen.

The targeting moiety T wherein the target cell is an osteoclast can be RANKL (receptor activator or NF-κβ ligand) or TNF-α, both of which are implicated in osteoclastogenesis. See Ritchlin et al., *J. Clinical Investigation* 111 (6), 821-831 (2003), "Mechanisms of TNF-α and RANKL-mediated Osteoclastogenesis and Bone Resorption in Psoriatic Arthritis"; Väänänen et al., *J. Cell Sci.* 113, 377-381 (2000), "The Cell Biology of Osteoclast Function"; and Rodan et al., *Science* 289, 1508-1514 (2000), "Therapeutic Approaches to Bone Diseases"; the disclosures of which are incorporated herein by reference.

Those skilled in the art will appreciate that bafilomycin $A_1$ also inhibits acidification of lysosomes (Yoshimori et al., *J. Biol. Chem.* 266 (26), 17707-17712 (1991), for which reason it may be desirable to avoid pH sensitive or acid hydrolase-cleavable linker moieties L in this particular embodiment and use instead other types of linker moieties L.

The method of treating the aforementioned diseases comprises administering a therapeutically effective amount of an inventive combination to a subject. The method may be repeated as necessary.

The practice of this invention can be further understood by reference to the following examples, which are provided by way of illustration and not of limitation.

EXAMPLE 1

FIG. 7 depicts the synthesis of maytansinoid compounds usable as modified active agents in conjugates of this invention, as detailed in this example. The preparation of maytansinoid conjugates is also described in Santi et al., US 2003/0109682 A1 (2003), the disclosure of which is incorporated herein by reference.

Maytansinol-3-bromoacetate (2). Maytansinol (1) is obtained by reduction of ansamitocin P3 (AP3), as described in Kupchan et al., *J. Am. Chem. Soc.*, 97, 5294-5295 (1975), and is then acylated according to the procedure of Kawai et al., *Chem. Pharm. Bull.*, 32, 1001-1002 (1984), the disclosure of both documents being incorporated herein by reference. A solution of maytansinol (1 eq.), bromoacetic acid (6 eq.), dicyclohexylcarbodiimide ("DCC") or N-(3-dimethylaminopropyl)-N'-ethylcarbodiimide ("EDC") (6 eq) and 4-dimethylaminopyridine ("DMAP") (2 eq) in dichloromethane is stirred at room temperature until maytansinol no longer persists by thin layer chromatography ("TLC") analysis. The crude product is purified by column chromatography to provide maytansinol 3-bromoacetate (2).

3-Bromoacetyl-20-desmethyl-maytansine (3). Treatment of maytansinol 3-bromoacetate (2) with *Bacillus megaterium* results in C20 demethylation to generate 3-bromoacetyl-20-desmethyl-maytansine, as described in Isawa et al., *J. Antibiotics*, 34 (12), 1587-1590 (1981), incorporated herein by reference.

20-Desmethyl-3-phosphonoacetylmaytansine (4). An Arbuzov type reaction is employed for the synthesis of phosphono compound (4), as described in Sekine et al., *J. Am. Chem. Soc.*, 100, 1001-1002 (1978), incorporated herein by reference. To a solution of 3-bromoacetyl-20-desmethyl-maytansine (3) (1 eq.) in anhydrous tetrahydrofuran ("THF") is added a solution of tris(trimethylsilyl)phosphite (2 eq.) in anhydrous THF. The reaction is stirred at room temperature until bromoacetate 3 no longer persists by TLC analysis. The solution is then treated with ethanol (3-5 eq.) and aniline (2-4 eq.) to hydrolyze the silyl phosphonate to phosphonic acid (4), which is usable as the modified active agent in conjugates such as those shown in formulae I, II, and III.

3-Trimethylammoniumacetyl-20-desmethylmaytansine (5). To a solution of 3-bromoacetyl-20-desmethyl-maytansine (3) (1 eq) in anhydrous THF is added a solution of trimethylamine (1.1 eq) in anhydrous THF. The reaction is stirred at room temperature until bromoacetate (3) no longer persists by TLC analysis. The product is isolated by concentration under reduced pressure. Trimethylammonium compound 5 is usable in conjugates such as those shown in formulae IV, V, and VI.

EXAMPLE 2

Figure 8:
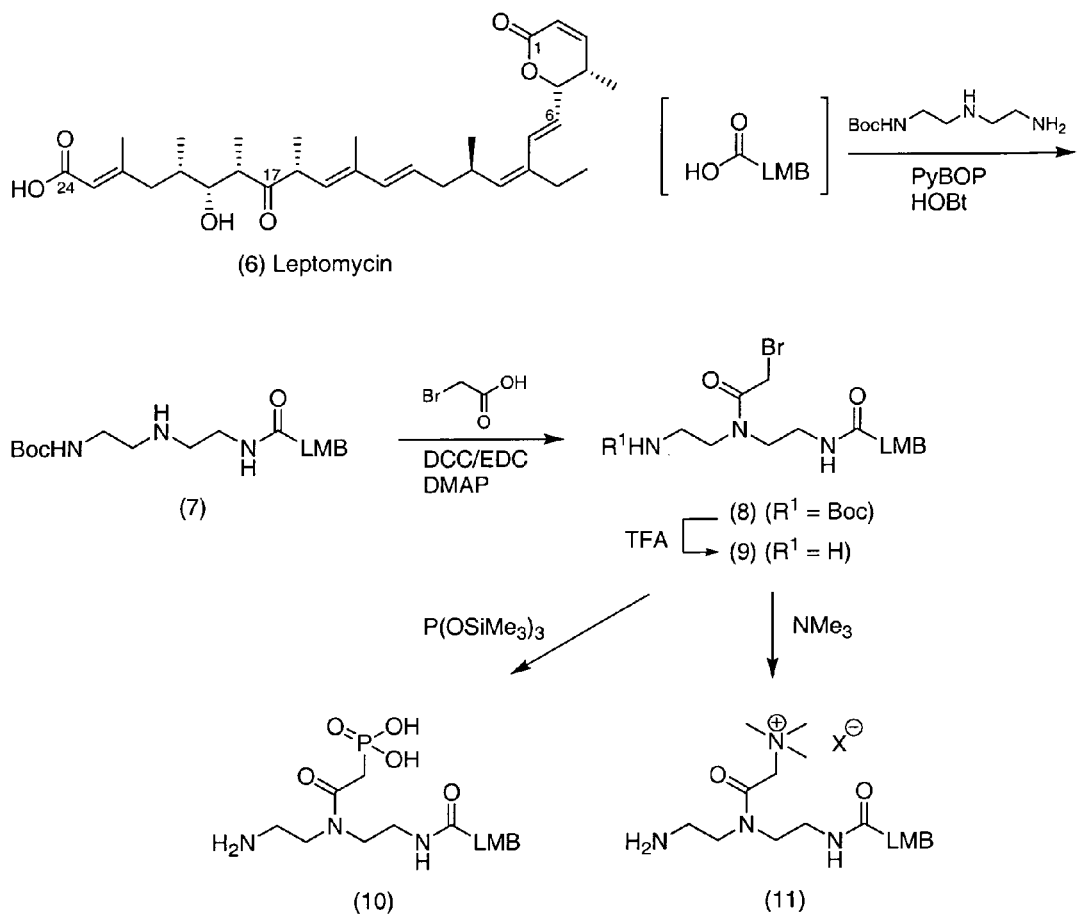
FIG. 8 shows the synthesis of leptomycin B compounds usable as modified active agents in conjugates of this invention.

FIG. 8 shows the synthesis of leptomycin B compounds usable as modified active agents in conjugates of this invention, as detailed in this example.

t-Butyloxycarbonyl ("Boc")-Protected amide (7). To a solution of diethylene triamine (1 eq) and sodium bicarbonate (2 eq) in THF-water is slowly added a solution of di-t-butyl dicarbonate ("$Boc_2O$") (1.0 eq) in THF. The reaction is stirred until judged complete by TLC analysis. The crude protected amine is then slowly added to a solution of leptomycin B (1.0 eq), benzotriazol-1-yloxy)tripyrrolidinophosphonium hexafluorophosphate ("PyBOP") (1.1 eq) and N-hydroxybenzotriazole ("HOBt") (1.1 eq) in N,N-dimethylformamide ("DMF"). This solution is stirred until judged complete by TLC analysis. The Boc-protected amide 7 can be isolated with column chromatography.

Bromoacetamide leptomycin B (8). A solution of amide 7 (1 eq), bromoacetic acid (6 eq), DCC or EDC (6 eq) and DMAP (2 eq) in dichloromethane is stirred at room temperature until amide 7 no longer persists by TLC analysis, to provide Boc-protected bromoacetyl derivative 8. After removal of the Boc protecting group with trifluoroacetic acid ("TFA") and purification by column chromatography, the desired bromoacetamide-modified LMB 9 is obtained.

Phosphono leptomycin B (10). An Arbuzov type reaction is employed for the synthesis of phosphonoacetamide leptomycins, as described above in Example 1. To a solution of bromoacetamide LMB derivative 9 (1 eq) in anhydrous THF is added a solution of tris(trimethylsilyl) phosphite (2 eq) in anhydrous THF. The reaction is stirred at rt until the bromoacetamide no longer persists by TLC analysis. The solution is then treated with ethanol (3-5 eq) and aniline (2-4 eq) to hydrolyze the silyl phosphonate to phosphonic acid, yielding phosphonic acid 10, which is usable in conjugates of this invention having structures according to formulae VII, VIII, and IX.

Trimethylammonium acetamide leptomycin B (11). To a solution of bromoacetamide leptomycin B 8 (1 eq) in anhydrous THF is added a solution of trimethylamine (1.5 eq) in anhydrous THF. The reaction is stirred at room temperature until the bromoacetamide no longer persists by TLC analysis. The product is isolated by concentration under reduced pressure, to yield an intermediate usable for making conjugates such as X, XI, and XII.

EXAMPLE 3

This example describes the preparation of maleimide linked conjugates.

MC-Val-Cit-PAB-OH is prepared as described in Dubowchik et al., *Bioconjugate Chem.*, 13, 855-869 (2002) ("Dubowchik et al.", incorporated herein by reference). (MC stands for a maleimidocaproyl moiety, Val stands for a valyl moiety, Cit stands for a citrullinyl moiety, and PAB stands for p-aminobenzyl.)

Ether-linked intermediates. Generally, active agents or modified active agents can be connected to linker moieties via an ether linkage according to the procedure of Toki et al., *J. Org. Chem.*, 67, 1866-1872 (2002) ("Toki et al.", incorporated herein by reference). The following detailed procedure is representative: Fmoc-Val-Cit-PABOH (Fmoc denoting a 9-fluorenylmethoxycarbonyl group; Dubowchik et al., *Bioconjugate Chem.*, 13, 855-869 (2002), 1 eq), triphenylphosphine (1.1 eq) and active agent or modified active agent having a phenolic OH group (1.1 eq) are dissolved in DMF: toluene (1:1) and evaporated to dryness under high vacuum. The residue is dissolved in anhydrous DMF under nitrogen. After cooling the reaction vessel in a 0° C. ice bath, neat diisopropyl azodicarboxylate ("DIAD") (1.1 eq) is added dropwise over a 1 min period. After warming to room temperature and stirring for 2-4 hr, additional triphenylphosphine (1.1 eq) and DIAD (1.1 eq) are added to the reaction. Stirring is continued at room temperature for 20 hr and then the solvent is removed under high vacuum. The resulting crude residue is purified by column chromatography using dichloromethane-methanol mobile phase to provide the advanced intermediate. A two-step sequence involving Fmoc deprotection and acylation with MC-OSu (OSu denoting an N-hydroxysuccinate group; Dubowchik et al.) is used to provide the desired active agent (or modified active agent) maleimide linker moiety intermediates.

Carbamate-linked intermediates. Generally, active agents or modified active agents can be connected to linker moieties via a carbamate linkage according to the procedure of Dubowchik et al. MC-Val-Cit-PABOH (1 eq) and bis-p-nitrophenyl carbonate (bis-PNP carbonate) (5 eq) are dissolved in anhydrous dichloromethane at room temperature under nitrogen. To this solution is added N-ethyldiisopropylamine ("DIPEA") (3 eq), and the reaction is stirred at room temperature for 3 days. The solution is then concentrated to near dryness, and the resulting residue is diluted with ethyl acetate and washed with phosphate buffer (pH 5), water and brine. The organic phase is then separated, dried over magnesium sulfate, filtered and concentrated under reduced pressure. The resulting solid is triturated with diethyl ether, filtered, washed with diethyl ether and finally purified by column chromatography. This intermediate p-nitrophenyl ("PNP") carbonate (1 eq) is dissolved in N-methylpyrrolidone ("NMP"). To this solution are sequentially added an active agent or modified active agent containing an amine group (1 eq) and DIPEA (1 eq). The reaction is stirred for 2 days at room temperature in the dark then diluted with ethyl acetate. This solution is washed with water (4x) and brine. The organic layer is then separated, dried over magnesium sulfate, filtered and concentrated under reduced pressure. The resulting residue is purified by column chromatography to provide the desired active agent (or modified active agent) carbamate linker moiety intermediates.

Preparation of maleimide linked conjugates. Antibodies or protein carriers (5-100 mg/mL) in phosphate buffered saline ("PBS") are reduced with dithiothreitol at 37° C. for 30 min. Separation of low molecular weight compounds is performed by size exclusion HPLC ("SEC"). Thiol content of the antibody is determined using 5,5'-dithiobis(2-nitrobenzoic acid) ("DTNB") according to the procedure of Riddles et al., *Anal. Biochem.*, 94, 75-81 (1979), incorporated herein by reference.

To a PBS solution of reduced antibody at 4° C. is added a solution of the active agent (or modified active agent)-linker moiety intermediate (either ether or carbamate) in acetonitrile such that the final solution is 20% acetonitirle/PBS (v/v). Approximately 10 mol % excess of the intermediate is used relative to the total number of thiols present on the antibody. After 1 hr at 4° C., excess cysteine (20 eq relative to intermediate) is added, and the solution is concentrated by ultrafiltration. Gel filtration is used to remove any low molecular weight impurities. This general procedure is usable for the synthesis of conjugates such as I, IV, VII and X.

EXAMPLE 4

This example describes the preparation of amide linked conjugates.

Fmoc-Val-Cit-PABOH was prepared according to the procedure of Dubowchik et al.

Ether linked intermediates. Ether-linked intermediates are prepared according to the procedure of Toki et al., with the following detailed procedure being representative. Fmoc-Val-Cit-PABOH (1 eq), triphenylphosphine (1.1 eq) and the phenolic drug (1.1 eq) are dissolved in DMF:toluene (1:1) and evaporated to dryness under high vacuum. The residue is dissolved in anhydrous DMF under nitrogen. After cooling the reaction vessel in a 0° C. ice bath, neat DIAD (1.1 eq) is added dropwise over a 1 min period. After warming to room temperature and stirring for 2-4 hr, additional triphenylphosphine (1.1 eq) and DIAD (1.1 eq) are added to the reaction. Stirring is continued at room temperature for 20 hr and then the solvent is removed under high vacuum. The resulting crude residue is purified by column chromatography using dichloromethane/methanol mobile phase to provide the intermediate.

Carbamate linked intermediates. Carbamate linked intermediates are prepared according to the procedure of Dubowchik et al. Fmoc-Val-Cit-PABOH (1 eq) and bis-PNP carbonate (5 eq) are dissolved in anhydrous dichloromethane at room temperature under nitrogen. To this solution is added DIPEA (3 eq), and the reaction is stirred at room temperature for 3 days. The solution is then concentrated to near dryness, and the resulting residue is diluted with ethyl acetate and washed with phosphate buffer (pH 5), water and brine. The organic phase is then separated, dried over magnesium sulfate, filtered and concentrated under reduced pressure. The resulting solid is triturated with diethyl ether, filtered, washed with diethyl ether and finally purified by column chromatography. This intermediate PNP carbonate (1 eq) is dissolved in NMP. To this solution are sequentially added the amine-containing drug (1 eq) and DIPEA (1 eq). The reaction is stirred for 2 days at room temperature in the dark then diluted with ethyl acetate. This solution is washed with water (4×) and brine. The organic layer is then separated, dried over magnesium sulfate, filtered and concentrated under reduced pressure. The resulting residue is purified by column chromatography to provide the desired active agent (or modified active agent)-linker moiety carbamate linked intermediate.

Antibodies or protein carriers (5-100 mg/mL) are activated according to the procedure of Trouet et al., *Proc. Nat'l Acad. Sci. USA*, 79, 626-629 (1982), incorporated by reference. Antibodies are dissolved in water (pH 7.5) and to this solution is added succinic (or glutaric) anhydride stepwise while maintaining the pH at 7.5. The succinylated protein is then extensively dialyzed against PBS, sterilized by filtration and maintained at 4° C.

After Fmoc-deprotection (see Dubowchik et al.), active agent (or modified active agent)-linker moiety intermediate (20 µmol) is added to the succinylated protein (50 mg, 5 mL of saline at 10 mg/mL). EDC (7.5 mg) is added, and the solution is maintained at 4° C. in dark for 4 hr. Additional EDC is added, and the solution is maintained at room temperature overnight. The solution is then concentrated by ultrafiltration, and gel filtration is used to remove any low molecular weight impurities. This general procedure can be used for the synthesis of conjugates such as II, V, VIII and XI.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

The invention claimed is:

1. A conjugate having a structure according to one of formulae X, XI, or XII:

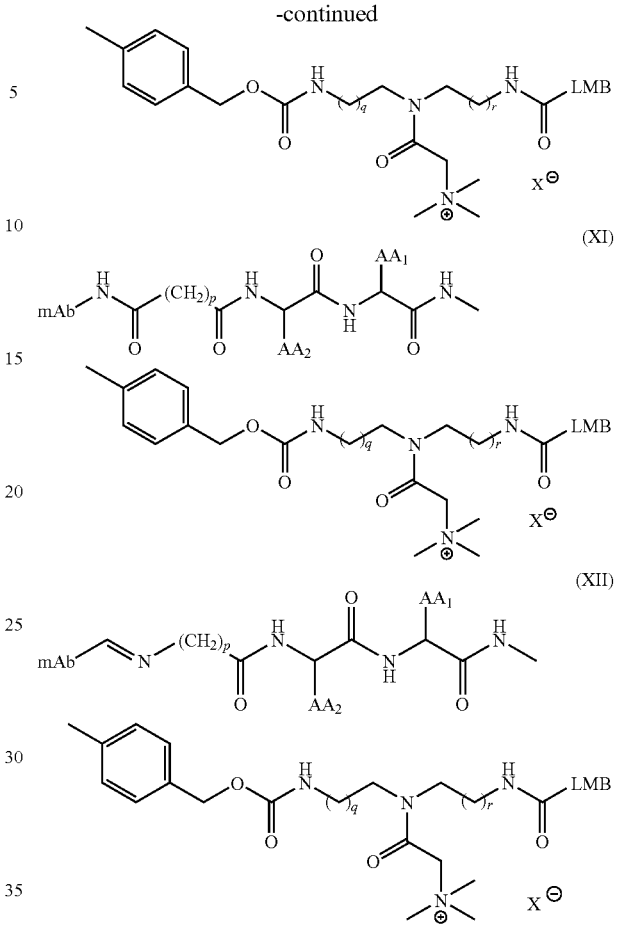

wherein
- $AA_1$ is a lysine, arginine, or citrulline amino acid side chain residue;
- $AA_2$ is a phenylalanine, valine, alanine, leucine, or isoleucine amino acid side chain residue;
- p in formulae X to XII is an integer from 1 to 6;
- q in formulae X to XII is an integer from 1 to 5;
- r in formulae X to XII is an integer from 1 to 5;
- —C(=O)LMB in formulae X to XII is a leptomycin B residue, having the structure

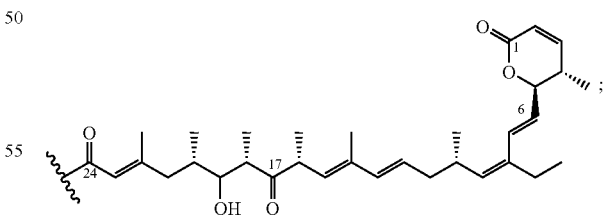

$x^\ominus$ in formulae X to XII is a pharmaceutically acceptable counteranion; and
mAb is a monoclonal antibody.

* * * * *

UNITED STATES PATENT AND TRADEMARK OFFICE
CERTIFICATE OF CORRECTION

PATENT NO.        : 7,541,330 B2                                             Page 1 of 1
APPLICATION NO. : 11/149758
DATED             : June 2, 2009
INVENTOR(S)       : Brian Hearn et al.

It is certified that error appears in the above-identified patent and that said Letters Patent is hereby corrected as shown below:

In the Claims:

At Column 21, Claim 1, Line 55 through 60 and Column 22, Line 2 through 35
Please delete all structures in Claim 1, in their entirety, and replace with the following full structures:

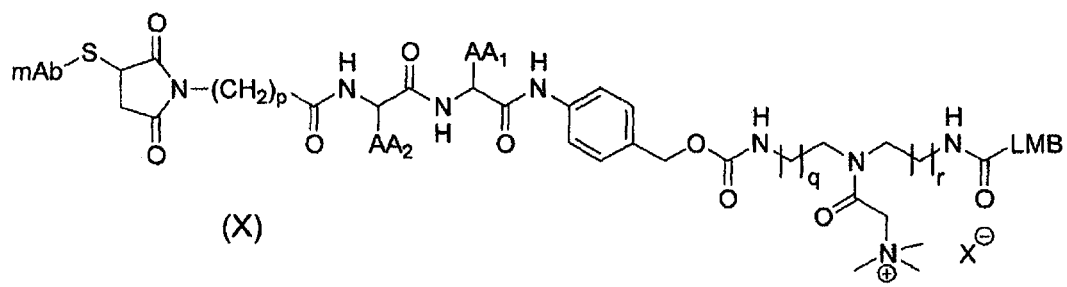

(X)

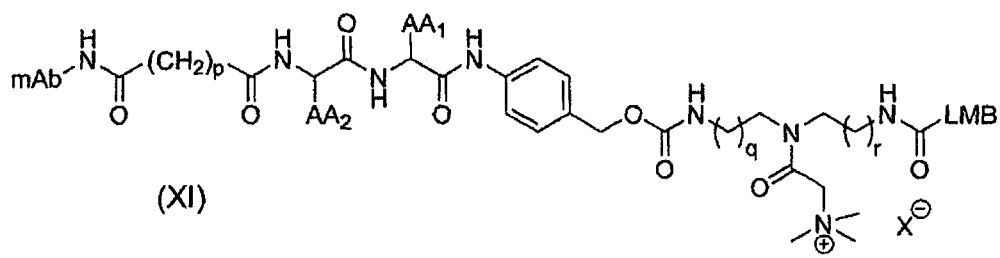

(XI)

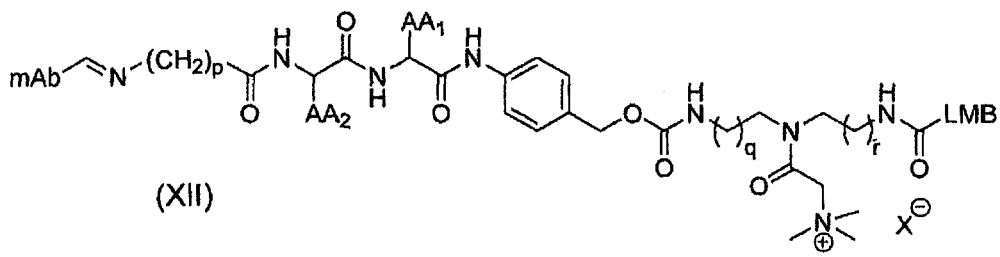

(XII)

Signed and Sealed this

Thirteenth Day of July, 2010

David J. Kappos
*Director of the United States Patent and Trademark Office*